April 17, 1956 G. L. BARKLEY Plant Pat. 1,470
APPLE TREE
Filed Aug. 28, 1953
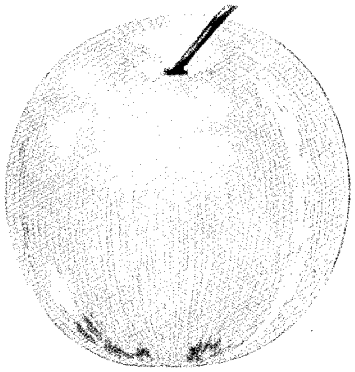
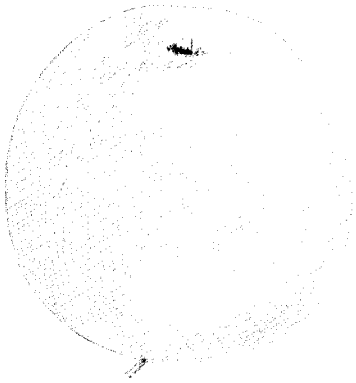
INVENTOR.
BY GEORGE L. BARKLEY
Reynolds, Beach & Christensen
ATTORNEYS United States Patent Office Plant Pat. 1,470
Patented Apr. 17, 1956

1,470

APPLE TREE

George L. Barkley, Chelan County, Wash., assignor to Van Well Nursery, Wenatchee, Wash., a copartnership Application August 28, 1953, Serial No. 377,271

1 Claim. (Cl. 47—62)

This invention or discovery relates to a new and distinct variety of apple tree, originating as a sport limb on a common Rome Beauty tree growing in my orchard at Manson, Washington, situated in the renowned Chelan-Wenatchee Valley apple growing area. This new variety has its nearest resemblance to the common Rome Beauty tree but has certain readily identified characteristics clearly distinguishing it therefrom as hereinafter described. The common Rome Beauty tree itself is an unpatented variety, dating back in origin more than one hundred years.

The common Rome Beauty tree produces good commercial fruit noted for its long-keeping qualities. However, its coloring is mediocre to poor, which reduces its popularity. The new and distinct variety herein described produces fruit having all of the desirable characteristics of the common Rome Beauty apple but with a distinctive and vastly superior skin coloring. The commercial potentialities of this improved variety are therefore exceptionally good.

The common Rome Beauty tree on which the original sport or mutation appeared and the stock upon which second, third and higher generation grafts have been made of the new variety developed from the original mutation, all grow in or immediately adjacent orchards in which the common Rome Beauty is grown commercially. Accordingly excellent opportunity was afforded for comparing the original and successive generations of the new variety with its nearest related variety. In general the new variety is similar to its parent, the common Rome Beauty tree, in all respects except the coloring of the fruit. The color of the common Rome Beauty apple varies from practically no color, that is a more or less greenish yellow, to a more or less mottled colored fruit with a bright red which in highly colored specimens deepens to almost solid red on the exposed cheek and is striped with a bright carmine. On the other hand the new variety has a yellow or greenish ground color with distinctive broad red stripes which develop into solid bright red or carmine color in highly colored fruits, with a chimera color formation developing in some specimens. This distinctive predominantly red and broadly striped fruit is very striking in appearance and should become highly popular. The fruit of this new variety with its chimeral striping is quite easily distinguished from both Cox's strain and Gallia Beauty strain of the Rome Beauty, as the latter strains have a solid or splashed type of color. Moreover, the latter strains do not attain as dark reds as the new variety.

The new variety has been asexually reproduced through successive generations by budding in my orchards at Manson, Washingtaon, and it clearly appears that its distinguishing characteristics are permanent.

The accompanying illustrations of the fruit of the new variety are as accurate as it is believed possible to make them; however it should be understood that the stripe formation and the depth and tone of color varies somewhat in different specimens.

The following is a detailed description of my new variety and is based on observations made of the original sport branch, of second and third generation grafts taken therefrom and applied to other stock, and of the fruit produced by such original branch and such grafts, grown in my orchard mentioned above:

TREE

A strong grower attaining a good medium size.

*Form.*—Upright at first but later roundish to somewhat spreading and drooping, with rather slender lateral branches.

*Twigs.*—Moderately stout, sometimes slender, moderately long; internodes short.

*Bark.*—Mottled brownish-red and green, rather bright.

*Lenticels.*—Deeply set in back, very short, broad, obtuse, oppressed.

*Leaves.*—Rather long, foliage not particularly robust.

FLOWERS

Similar to common Rome Beauty growing in same area, both as to appearance and as to dates of first and full bloom.

FRUIT

Medium to very large, usually averaging above medium, fairly uniform in size and shape.

*Form.*—Roundish to roundish conic or slightly oblong, regular or faintly ribbed, usually symmetrical but sometimes with sides unequal.

*Stem.*—Characteristically long, slender, and often oblique.

*Cavity.*—Medium to rather large, characteristically obtuse and smooth, moderately shallow to rather deep, wide, sometimes compressed or lipped, often gently furrowed, green or red, never russeted.

*Calyx.*—Rather small to medium, closed or somewhat open; lobes usually converging above but slightly separated toward the base.

*Basin.*—Small to medium, shallow to moderately deep, narrow to medium in width, sometimes abrupt, usually a little furrowed or wrinkled.

*Skin.*—Thick, tough, smooth, yellow or greenish, with broad red stripes which develop into solid bright red or carmine color on highly colored fruits. A chimera color formation develops on approximately sixty-five percent of the fruit, which adds to its attractiveness. Dots numerous and small at calxy end, more scattered and larger toward stem end; whitish or brownish in color. With more specific reference to color, a careful comparison was made of the fruits of the new variety with the color plates presented in the book, "Color Standards and Color Nomenclature" by Robert Ridgeway, 1912, Press of A. Hoen & Company, Baltimore, Maryland. It was found that the main color of the fruit compared to the "Carmine" color in Plate 1, whereas, the color of the Chimeras compared to "Old Rose" in Plate 13. The amount of the color in the Chimeras varies, so that some Chimeras appears darker than others. On ten percent of the examined fruits showing Chimeras, the Chimeras were twelve millimeters or more in width up to twenty-five millimeters. The remaining ninety percent of the fruits having Chimeras showed Chimeral bands less than twelve millimeters in width down to one millimeter in width. Sixty-five percent of the fruit have the chimeral stripe.

*Calyx tube.*—Cone-shape or approaching short truncate funnel-form, often with fleshy pistil point projecting into the base. Stamens: Marginal to median.

*Core.*—Medium to large, abaxile; cells sometimes unsymmetrical, open; core lines meeting or slightly clasping. Carpels: Roundish to ovate, narrowing both toward base and apex, sometimes obtusely emarginate, mucronate, sometimes tufted. Seeds: Numerous, medium in size, plump, acute to somewhat obtuse, slightly tufted, light and dark brown.

*Flesh.*—Nearly white with slight tinge of yellow, firm, moderately fine-grained to a little coarse, rather crisp, juicy, slightly aromatic, agreeably mild subacidic.

*Keeping qualities.*—Excellent.

*Maturity season, resistance to disease and severe weather, care requirements, etc.*—Similar to common Rome Beauty.

Having thus disclosed by improved invention or discovery, I claim:

The new and distinct variety of apple tree, characterized as to novelty primarily by the coloring of its fruit by which it is distinguished from the nearest related variety, the common Rome Beauty, substantially as shown and described.

No references cited.